US 6,582,370 B2

(12) United States Patent
Jibiki (10) Patent No.: US 6,582,370 B2
(45) Date of Patent: Jun. 24, 2003

(54) BLOOD FLOW IMAGING METHOD, BLOOD FLOW IMAGING APPARATUS AND ULTRASONIC DIAGNOSTIC APPARATUS

(75) Inventor: Takao Jibiki, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 31 days.

(21) Appl. No.: 10/034,850

(22) Filed: Dec. 27, 2001

(65) Prior Publication Data
US 2002/0103437 A1 Aug. 1, 2002

(30) Foreign Application Priority Data
Feb. 1, 2001 (JP) ........................................ 2001-025716

(51) Int. Cl.⁷ ................................................ A61B 8/00
(52) U.S. Cl. ...................... 600/455; 600/454; 600/458; 600/438
(58) Field of Search ................................. 600/454, 455, 600/458, 453, 437, 438

(56) References Cited

U.S. PATENT DOCUMENTS

| 5,255,683 A | * | 10/1993 | Monaghan | ................. | 600/458 |
| 5,513,640 A | * | 5/1996 | Yamazaki et al. | .......... | 600/455 |
| 5,615,680 A | * | 4/1997 | Sano | ........................ | 600/437 |
| 5,634,465 A | * | 6/1997 | Schmiesing et al. | ........ | 600/454 |
| 5,749,364 A | * | 5/1998 | Silwa et al. | ................. | 600/438 |

* cited by examiner

Primary Examiner—Marvin M. Lateef
Assistant Examiner—Ruby Jain
(74) Attorney, Agent, or Firm—Moonray Kojima (57) ABSTRACT

In order to properly discern a plurality of streams of blood flow having different contrast agent arrival times or blood concentration properties, an ultrasonic diagnostic apparatus 200 comprises: an ultrasonic probe 1; a transceiver section 2; a quadrature detector section 3; a power calculating section 4 for calculating the power P of blood flow; a power peak holding section 21 for comparing the latest power P and a predecessor peak value Po, and outputting the larger one as a peak value P' and an elapsed time t' corresponding to the peak value P'; a predecessor power/elapsed time keeping section 22 for keeping the predecessor peak value Po and the corresponding elapsed time 'to' and outputting these values to the power peak holding section 21; a timer 11 for measuring an elapsed time t from a reference time; a blood flow image producing section 25 for producing a power peak hold blood flow image G2 in which the hue is changed before and after the elapsed time t' reaches a hue change time tc and the brightness varies depending upon the peak value P'; an operating section 12 for resetting the timer 11 and specifying the hue change time tc; and a display 6. For example, blood flow passing through the hepatic artery and that passing through the portal vein can be displayed in different colors.

22 Claims, 12 Drawing Sheets

FIG. 6A
Blood flow image
G1 (t1)

FIG. 6B
Blood flow image
G1 (tc)

FIG. 6C
Blood flow image
G1 (t2)

In-flow threshold hold mode blood flow image

In-flow threshold hold mode blood flow image

In-flow threshold hold mode blood flow image

Out-flow threshold hold
mode blood flow image
G4 (t1)

FIG. 14B

Out-flow threshold hold
mode blood flow image
G4 (tc)

FIG. 14C

Out-flow threshold hold
mode blood flow image
G4 (t2)

FIG. 15A

Blood flow image
G1 (t1)

Hepatic artery
(Bright red)
α2

FIG. 15B

Blood flow image
G1 (t2)

Hepatic artery
(Bright blue)
α2

Portal vein
(Bright blue)
β2

Superimpose

FIG. 15C

Superimposition mode
blood flow image
G5

Hepatic artery
(Bright purple)
α2

Portal vein
(Bright blue)

Monochrome mode
blood flow image
<u>G6</u> (t = t1)

FIG. 17B

Monochrome mode
blood flow image
<u>G6</u> (t = tc')

FIG. 17C

Monochrome mode
blood flow image
<u>G6</u> (t = t2)

FIG. 18

BLOOD FLOW IMAGING METHOD, BLOOD FLOW IMAGING APPARATUS AND ULTRASONIC DIAGNOSTIC APPARATUS

BACKGROUND OF THE INVENTION

The present invention relates to a blood flow imaging method, blood flow imaging apparatus and ultrasonic diagnostic apparatus, and more particularly to a blood flow imaging method, blood flow imaging apparatus and ultrasonic diagnostic apparatus by which a plurality of streams of blood flow having different contrast agent arrival times or blood concentration properties can be properly discerned.

RELATED ART

Figure 1:
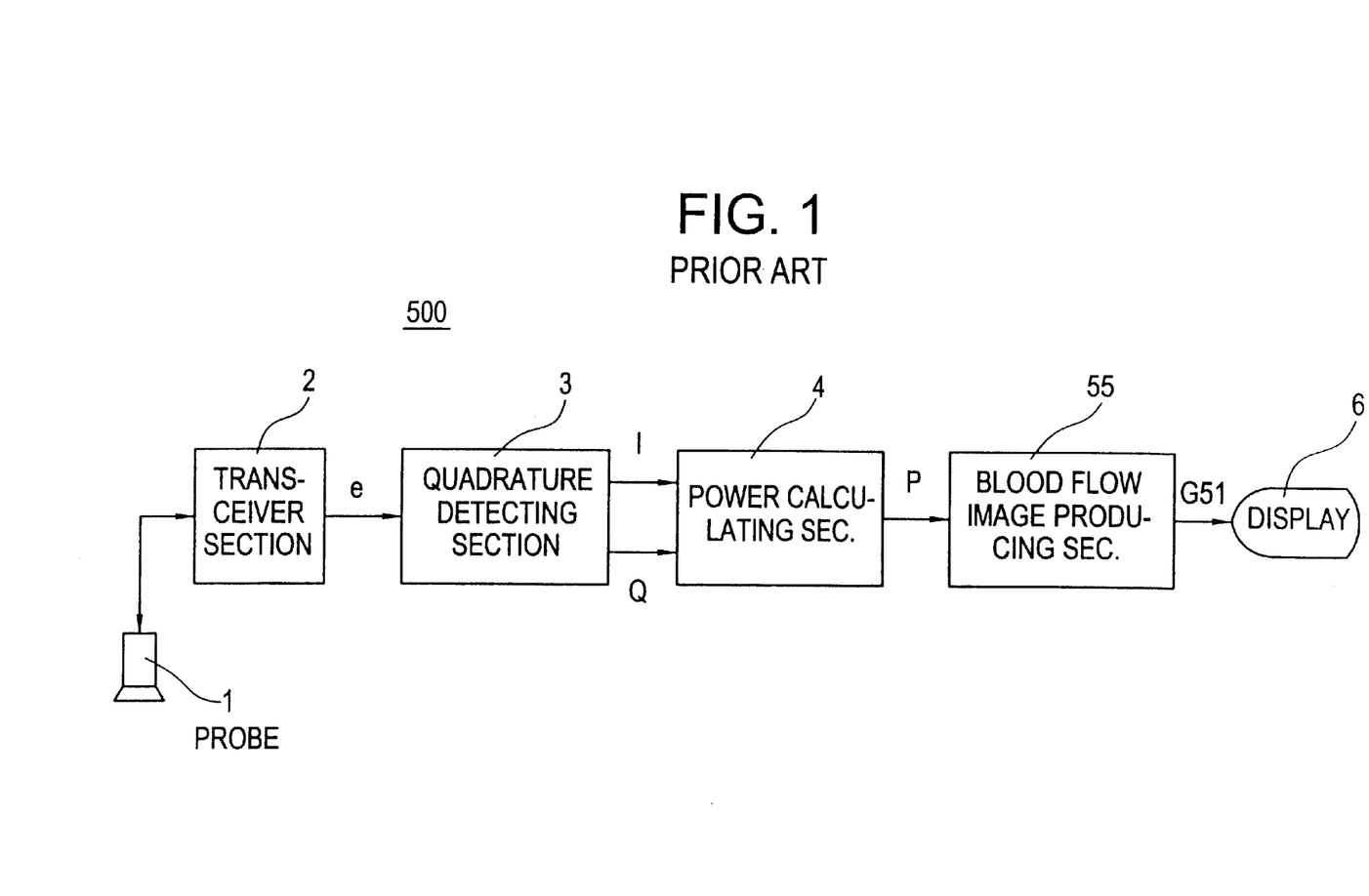
FIG. 1 is a block diagram showing an example of a conventional ultrasonic diagnostic apparatus.

FIG. 1 is a block diagram showing an example of a conventional ultrasonic diagnostic apparatus having a power Doppler mode.

The ultrasonic diagnostic apparatus 500 comprises: an ultrasonic probe 1; a transceiver section 2 for transmitting ultrasound from the ultrasonic probe 1, acquiring an ultrasonic echo and outputting a received signal based on the ultrasonic echo; a quadrature detector section 3 for outputting in-phase (I) and quadrature (Q) components of the received signal e; a power calculating section 4 for calculating the power P of blood flow; a blood flow image producing section 55 for producing a blood flow image G51 in which the brightness varies depending upon the power P; and a display 6. The blood flow image G51 is displayed in, for example, orange of higher brightness for the larger power P.

When a contrast agent (microballoons) is intravenously injected into a subject, blood flow infused with the contrast agent is represented. In imaging the liver, for example, as the contrast agent carried by the blood flow reaches the hepatic artery and the portal vein, the blood flow streams passing through these blood vessels are represented.

In the conventional ultrasonic diagnosis apparatus 500, there is a problem that, for example, the blood flow passing through the hepatic artery and that passing through the portal vein are displayed overlapping each other on a screen, and they are difficult to properly distinguish.

SUMMARY OF THE INVENTION

It is therefore an object of the present invention to provide a blood flow imaging method, blood flow imaging apparatus and ultrasonic diagnostic apparatus by which a plurality of streams of blood flow having different contrast agent arrival times or blood concentration properties can be properly discerned.

In accordance with a first aspect, the present invention provides a blood flow imaging method for scanning and detecting blood flow infused with a contrast agent injected into a subject, and displaying the blood flow, comprising: changing at least one of the hue and gradation range of a display region representing the blood flow in one or more steps in the course of time.

In the blood flow imaging method of the first aspect, since the hue or display gradation of a blood flow image is changed relative to time, a plurality of streams of blood flow having different arrival times of a contrast agent can be properly discerned.

In accordance with a second aspect, the present invention provides a blood flow imaging method for scanning and detecting blood flow infused with a contrast agent injected into a subject, and displaying the blood flow, comprising: displaying a plurality of streams of blood flow having different times at which the blood flow detection intensity reaches a peak value, in different hues or gradation ranges.

In the blood flow imaging method of the second aspect, even if a time period in which a plurality of streams of blood flow are simultaneously infused with the contrast agent is long, the hues or display gradations of the blood flow streams can be differentiated based upon the difference of the time at which the blood flow detection intensity, or the blood concentration of the contrast agent, reaches a peak value.

In accordance with a third aspect, the present invention provides a blood flow imaging method for scanning and detecting blood flow infused with a contrast agent injected into a subject, and displaying the blood flow, comprising: displaying the blood flow in a predefined hue or gradation range before a hue etc. change time specified within a contrast agent flow-in period, and displaying, after the hue etc. change time, the blood flow in a hue or gradation range determined based on the relationship between the blood flow detection intensity and an in-flow threshold at the hue etc. change time.

In the blood flow imaging method of the third aspect, since the hue or gradation range for the time after the hue etc. change time is determined based on the relationship between the blood flow detection intensity and an in-flow threshold at the hue etc. change time, even if the arrival times or the blood concentration properties of the contrast agent are similar among a plurality of streams of blood flow, the hues or display gradations of the blood flow streams can be differentiated based upon the difference of the in-flow properties of the contrast agent.

In accordance with a fourth aspect, the present invention provides a blood flow imaging method for scanning and detecting blood flow infused with a contrast agent injected into a subject, and displaying the blood flow, comprising: displaying the blood flow in a predefined hue or gradation range before a hue etc. change time specified within a contrast agent flow-out period, and displaying, after the hue etc. change time, the blood flow in a hue or gradation range determined based on the relationship between the blood flow detection intensity and an out-flow threshold at the hue etc. change time.

In the blood flow imaging method of the fourth aspect, since the hue or gradation range for the time after the hue etc. change time is determined based on the relationship between the blood flow detection intensity and an out-flow threshold at the hue etc. change time, even if the arrival times or the blood concentration properties of the contrast agent are similar among a plurality of streams of blood flow, the hues or display gradations of the blood flow streams can be differentiated based upon the difference of the out-flow properties of the contrast agent.

In accordance with a fifth aspect, the present invention provides a blood flow imaging method for scanning and detecting blood flow infused with a contrast agent injected into a subject, and displaying the blood flow, comprising: producing a plurality of blood flow images corresponding to different times in different hues or gradation ranges, and displaying a blood flow image in which the plurality of blood flow images are superimposed.

In the blood flow imaging method of the fifth aspect, since a plurality of blood flow images having different hues or gradation ranges depending upon the time are superimposed, a plurality of streams of blood flow having different arrival times of the contrast agent can be displayed in different colors or gradations on one still image, and visibility is improved.

In accordance with a sixth aspect, the present invention provides a blood flow imaging apparatus comprising: scanning means for scanning a subject to detect blood flow infused with a contrast agent; blood flow image producing means for producing a blood flow image in which at least one of the hue and gradation range of a display region representing the blood flow is changed in one or more steps in the course of time; and blood flow image displaying means for displaying the blood flow image.

In the blood flow imaging apparatus of the sixth aspect, the blood flow imaging method of the first aspect can be suitably implemented.

In accordance with a seventh aspect, the present invention provides a blood flow imaging apparatus comprising: scanning means for scanning a subject to detect blood flow infused with a contrast agent; blood flow image producing means for producing a blood flow image in which a plurality of streams of blood flow having different times at which the blood flow detection intensity reaches a peak value are represented in different hues or gradation ranges; and blood flow image displaying means for displaying the blood flow image.

In the blood flow imaging apparatus of the seventh aspect, the blood flow imaging method of the second aspect can be suitably implemented.

In accordance with an eighth aspect, the present invention provides a blood flow imaging apparatus comprising: scanning means for scanning a subject to detect blood flow infused with a contrast agent; hue etc. change time specifying means for use by an operator to specify a hue etc. change time within a contrast agent in-flow period; blood flow image producing means for producing a blood flow image in which the blood flow is represented in a predefined hue or gradation range before the hue etc. change time, and producing a blood flow image in which the blood flow is represented, after the hue etc. change time, in a hue or gradation range determined based on the relationship between the blood flow detection intensity and an in-flow threshold at the hue etc. change time; and blood flow image displaying means for displaying the blood flow image.

In the blood flow imaging apparatus of the eighth aspect, the blood flow imaging method of the third aspect can be suitably implemented.

In accordance with a ninth aspect, the present invention provides a blood flow imaging apparatus comprising: scanning means for scanning a subject to detect blood flow infused with a contrast agent; hue etc. change time specifying means for use by an operator to specify a hue etc. change time within a contrast agent out-flow period; blood flow image producing means for producing a blood flow image in which the blood flow is represented in a predefined hue or gradation range before the hue etc. change time, and producing a blood flow image in which the blood flow is represented, after the hue etc. change time, in a hue or gradation range determined based on the relationship between the blood flow detection intensity and an out-flow threshold at the hue etc. change time; and blood flow image displaying means for displaying the blood flow image.

In the blood flow imaging apparatus of the ninth aspect, the blood flow imaging method of the fourth aspect can be suitably implemented.

In accordance with a tenth aspect, the present invention provides a blood flow imaging apparatus comprising: scanning means for scanning a subject to detect blood flow infused with a contrast agent; blood flow image producing means for producing a plurality of blood flow images corresponding to different times in different hues or gradation ranges, and producing a blood flow image in which the plurality of blood flow images are superimposed; and blood flow image displaying means for displaying the superimposed blood flow image.

In the blood flow imaging apparatus of the tenth aspect, the blood flow imaging method of the fifth aspect can be suitably implemented.

In accordance with an eleventh aspect, the present invention provides an ultrasonic diagnostic apparatus comprising: an ultrasonic probe; a transceiver section for transmitting ultrasound from the ultrasonic probe, acquiring an ultrasonic echo and outputting a received signal based on the ultrasonic echo; blood flow image producing means for, based on the received signal, producing a blood flow image in which at least one of the hue and gradation range of a display region representing blood flow infused with a contrast agent is changed in one or more steps in the course of time; and blood flow image displaying means for displaying the blood flow image.

In the ultrasonic diagnostic apparatus of the eleventh aspect, the blood flow imaging method of the first aspect can be suitably implemented.

In accordance with a twelfth aspect, the present invention provides an ultrasonic diagnostic apparatus comprising: an ultrasonic probe; a transceiver section for transmitting ultrasound from the ultrasonic probe, acquiring an ultrasonic echo and outputting a received signal based on the ultrasonic echo; blood flow image producing means for, based on the received signal, producing a blood flow image in which a plurality of streams of blood flow having different times at which the blood flow detection intensity reaches a peak value are represented in different hues or gradation ranges; and blood flow image displaying means for displaying the blood flow image.

In the ultrasonic diagnostic apparatus of the twelfth aspect, the blood flow imaging method of the second aspect can be suitably implemented.

In accordance with a thirteenth aspect, the present invention provides an ultrasonic diagnostic apparatus comprising: an ultrasonic probe; a transceiver section for transmitting ultrasound from the ultrasonic probe, acquiring an ultrasonic echo and outputting a received signal based on the ultrasonic echo; hue etc. change time specifying means for use by an operator to specify a hue etc. change time within a contrast agent in-flow period; blood flow image producing means for, based on the received signal, producing a blood flow image in which the blood flow is represented in a predefined hue or gradation range before the hue etc. change time, and producing a blood flow image in which the blood flow is represented, after the hue etc. change time, in a hue or gradation range determined based on the relationship between the blood flow detection intensity and an in-flow threshold at the hue etc. change time; and blood flow image displaying means for displaying the blood flow image.

In the ultrasonic diagnostic apparatus of the thirteenth aspect, the blood flow imaging method of the third aspect can be suitably implemented.

In accordance with a fourteenth aspect, the present invention provides an ultrasonic diagnostic apparatus comprising: an ultrasonic probe; a transceiver section for transmitting ultrasound from the ultrasonic probe, acquiring an ultrasonic echo and outputting a received signal based on the ultrasonic echo; hue etc. change time specifying means for use by an operator to specify a hue etc. change time within a contrast agent out-flow period; blood flow image producing means for, based on the received signal, producing a blood flow image in which the blood flow is represented in a predefined hue or gradation range before the hue etc. change time, and producing a blood flow image in which the blood flow is represented, after the hue etc. change time, in a hue or gradation range determined based on the relationship between the blood flow detection intensity and an out-flow threshold at the hue etc. change time; and blood flow image displaying means for displaying the blood flow image.

In the ultrasonic diagnostic apparatus of the fourteenth aspect, the blood flow imaging method of the fourth aspect can be suitably implemented.

In accordance with a fifteenth aspect, the present invention provides an ultrasonic diagnostic apparatus comprising: an ultrasonic probe; a transceiver section for transmitting ultrasound from the ultrasonic probe, acquiring an ultrasonic echo and outputting a received signal based on the ultrasonic echo; blood flow image producing means for, based on the received signal, producing a plurality of blood flow images corresponding to different times in different hues or gradation ranges, and producing a blood flow image in which the plurality of blood flow images are superimposed; and blood flow image displaying means for displaying the superimposed blood flow image.

In the ultrasonic diagnostic apparatus of the fifteenth aspect, the blood flow imaging method of the fifth aspect can be suitably implemented.

In accordance with a sixteenth aspect, the present invention provides the ultrasonic diagnostic apparatus of the aforementioned configuration, wherein the blood flow image producing means produces the blood flow image synchronously with an electrocardiogram.

In the ultrasonic diagnostic apparatus of the sixteenth aspect, the blood flow image can be produced synchronously with the cardiac cycle.

According to the blood flow imaging method, blood flow imaging apparatus and ultrasonic diagnostic apparatus of the present invention, a plurality of streams of blood flow having different contrast agent arrival times or blood concentration properties can be displayed in different colors or gradations. Therefore, in diagnosing hepatoma, for example, the hepatic artery (blood flow in an artery system) and the portal vein (blood flow in a vein system) can be easily discerned, and discrimination between malignant and benign tumors and determination of the degree of differentiation can be achieved more exactly.

Moreover, blood flow corresponding to a plurality of times can be combined and displayed in one still image, and the efficiency in interpretation of the image by a physician can be improved.

Further objects and advantages of the present invention will be apparent from the following description of the preferred embodiments of the invention as illustrated in the accompanying drawings.

DETAILED DESCRIPTION OF THE INVENTION

The present invention will now be described in more detail with reference to several embodiments shown in the accompanying drawings. It should be noted that the present invention is not limited to these embodiments.

First Embodiment

Figure 2:
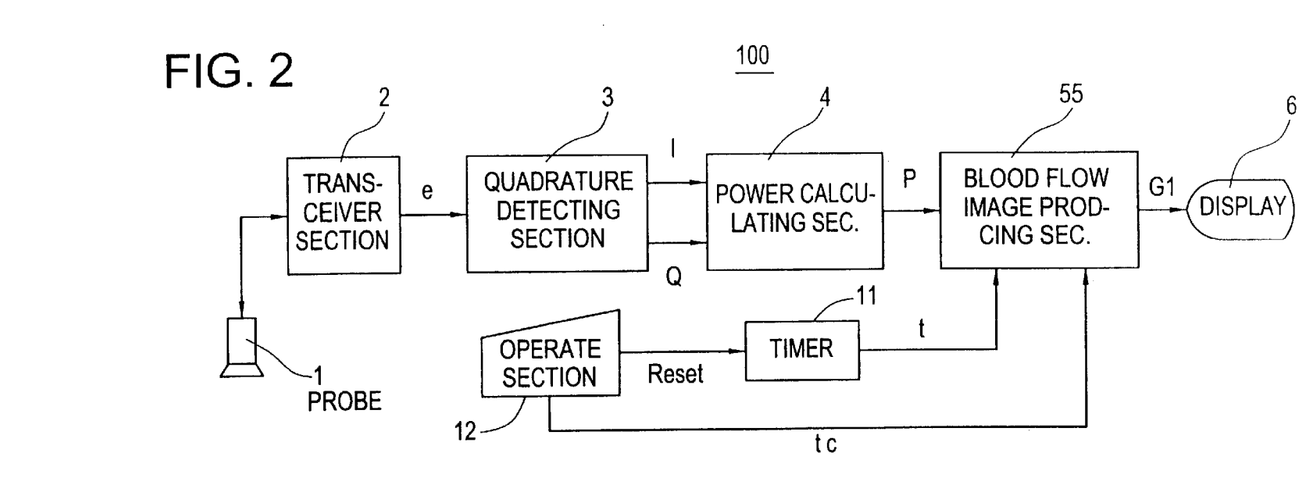
FIG. 2 is a block diagram showing an ultrasonic diagnostic apparatus in accordance with a first embodiment.

FIG. 2 is a block diagram showing an ultrasonic diagnostic apparatus in accordance with a first embodiment of the present invention.

The ultrasonic diagnostic apparatus 100 comprises: an ultrasonic probe 1; a transceiver section 2 for transmitting ultrasound from the ultrasonic probe 1, acquiring an ultrasonic echo and outputting a received signal e based on the ultrasonic echo; a quadrature detector section 3 for outputting in-phase (I) and quadrature (Q) components of the received echo signal e; a power calculating section 4 for calculating the power P of blood flow, i.e., calculating the sum of squares of the in-phase and quadrature components I and Q; a timer 11 for measuring an elapsed time t from a reference time; a blood flow image producing section 5 for producing a blood flow image G1 in which the hue is changed before and after the elapsed time t reaches a hue change time tc and the brightness varies depending upon the power P; an operating section 12 for resetting the timer 11 and specifying the hue change time tc; and a display 6 such as a CRT (cathode ray tube) device.

Figure 3:
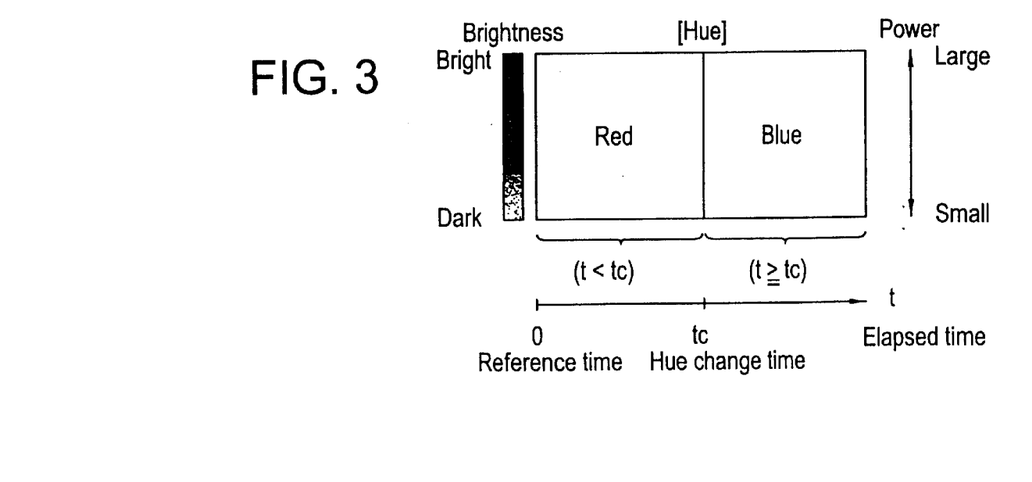
FIG. 3 is an explanatory diagram showing the hue of a blood flow image in the ultrasonic diagnostic apparatus of FIG. 2.

Specifically, the blood flow image producing section 5 sets the hue to 'Red' in a period t<tc and to 'Blue' in a period t≧tc, and raises the brightness of the color as the power P becomes larger, as shown in FIG. 3. It should be noted that two or more hue change times tc may be specified. For example, it is possible to specify hue change times tc1 and tc2 (tc<tc2), set the hue to 'Red' in a period t<tc1, to 'Yellow' in a period tc1≦t<tc2, and to 'Blue' in a period t≧tc2.

Figure 4:
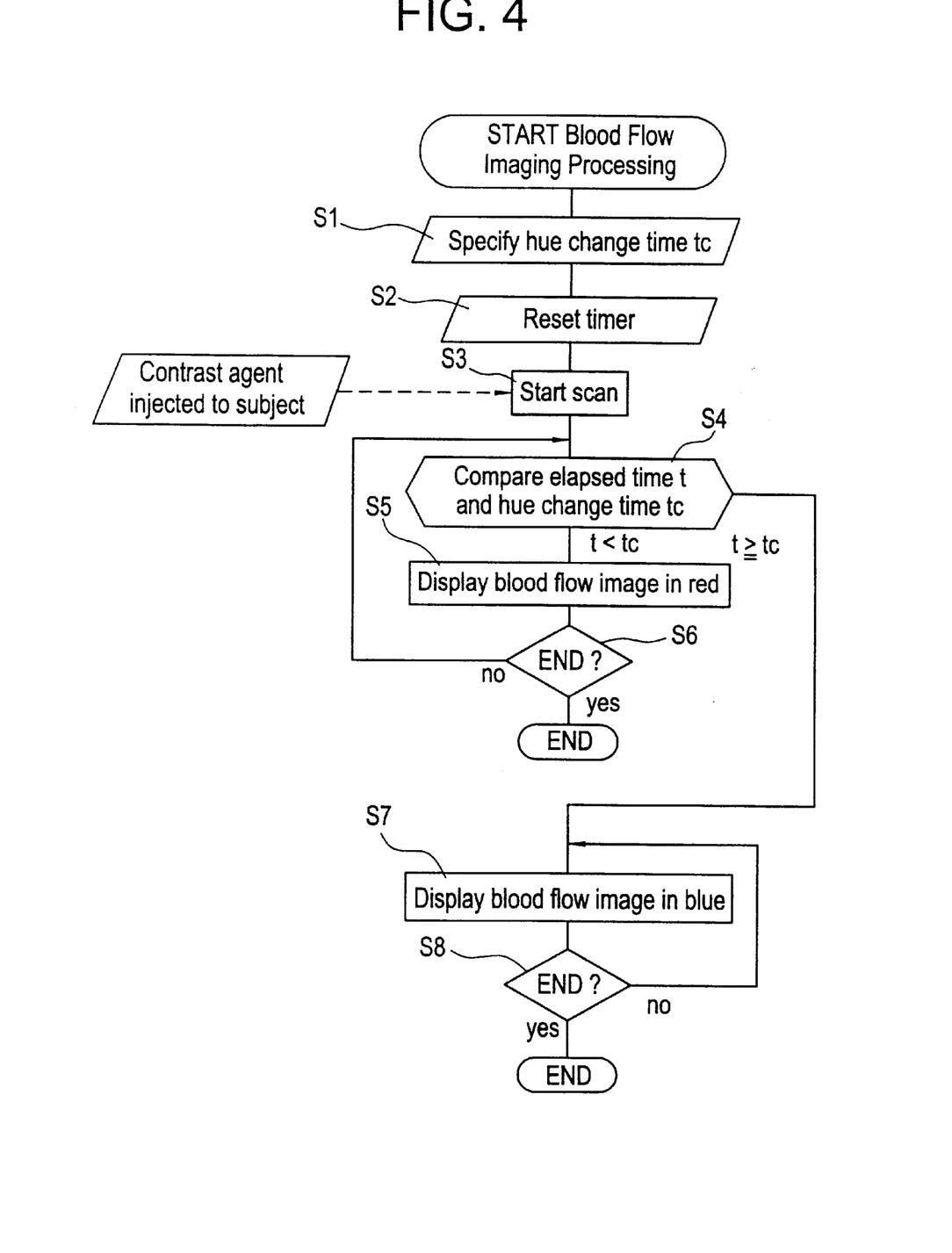
FIG. 4 is a flow chart showing blood flow imaging processing by the ultrasonic diagnostic apparatus of FIG. 2.

FIG. 4 is a flow chart showing blood flow imaging processing by the ultrasonic diagnostic apparatus 100 of FIG. 2.

In Step S1, an operator (ordinarily, a physician or a technician) specifies the hue change time tc using the operating section 12. Although the hue change time tc may be different depending upon the object blood flow, it is empirically determined in a range between, for example, several seconds and ten seconds or more. The hue change time tc may be specified or changed after starting a scan (after Step S3 below).

In Step S2, the operator resets the timer 11 using the operating section 11. The timer 11 measures an elapsed time t after the resetting.

In Step S3, a scan of the interior of the subject is started.

A contrast agent is injected into the subject immediately after Step S2, or immediately before or after Step S3.

In Step S4, the process goes to Step S5 in a period t<tc, and when t≧tc is reached, the process goes to Step S7.

In Step S5, the blood flow image producing section 5 produces a blood flow image G1 in red and displays the image G1 on the display 6.

In Step S6, if the termination of the process is not prescribed, the process goes back to Step S4; otherwise, the process is terminated.

In Step S7, the blood flow image producing section 5 produces the blood flow image G1 in blue and displays the image G1 on the display 6.

In Step S8, if the termination of the process is not prescribed, the process goes back to Step S7; otherwise, the process is terminated.

Figure 5:
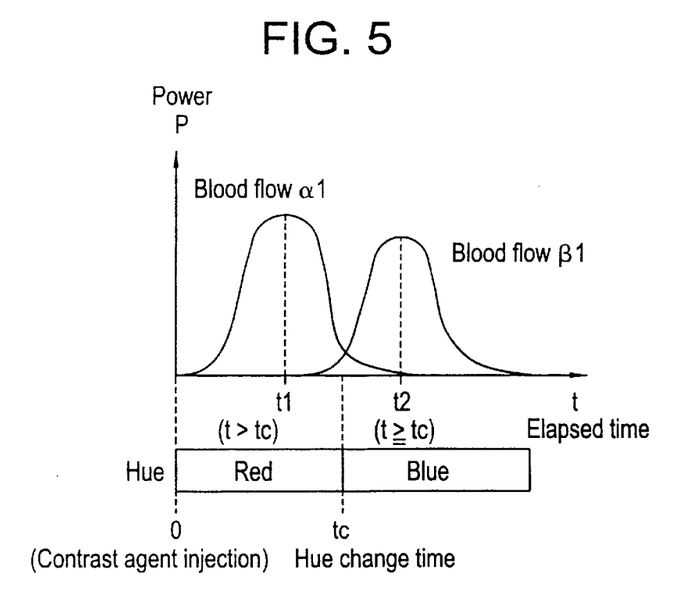
FIG. 5 is an explanatory diagram showing the relationship between the blood flow power properties and the hue of a blood flow image in the ultrasonic diagnostic apparatus of FIG. 2.

FIG. 5 shows an example of the properties of the power P of blood flow α1 and blood flow β1 and the hue with respect to the elapsed time t. It should be noted that the power P varies depending upon the blood concentration of the contrast agent.

Figures 6A, 6B:
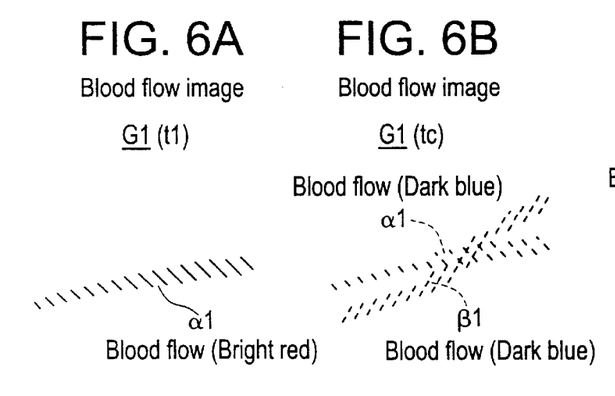
FIG. 6 is an explanatory diagram showing the transition of a blood flow image in the ultrasonic diagnostic apparatus of FIG. 2.

In the period t<tc, a blood flow image G1 in which the power P of the blood flow α1 and β1 is reflected is displayed in red. For example, at an elapsed time t1 at which the power P of the blood flow α1 reaches a peak value, the blood flow α1 is displayed in bright red, as shown in FIG. 6(a).

Figure 6C:
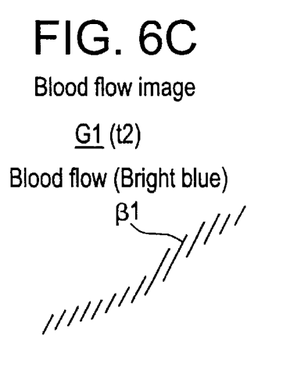

In the period t≧tc, a blood flow image G1 in which the power P of the blood flow α1 and β1 is reflected is displayed in blue. For example, at the elapsed time t=tc, the blood flow α1 and β1 are displayed in dark blue, as shown in FIG. 6(b). At an elapsed time t2 at which the power P of the blood flow β1 reaches a peak value, the blood flow β1 is displayed in bright blue, as shown in FIG. 6(c).

According to the ultrasonic diagnostic apparatus 100 of the first embodiment, since a blood flow image G1 in which the hue is changed before and after the elapsed time t reaches the hue change time tc is displayed, blood flow α1 and blood flow β1 having different arrival times of the contrast agent can be properly discerned.

Second Embodiment

Figure 7:
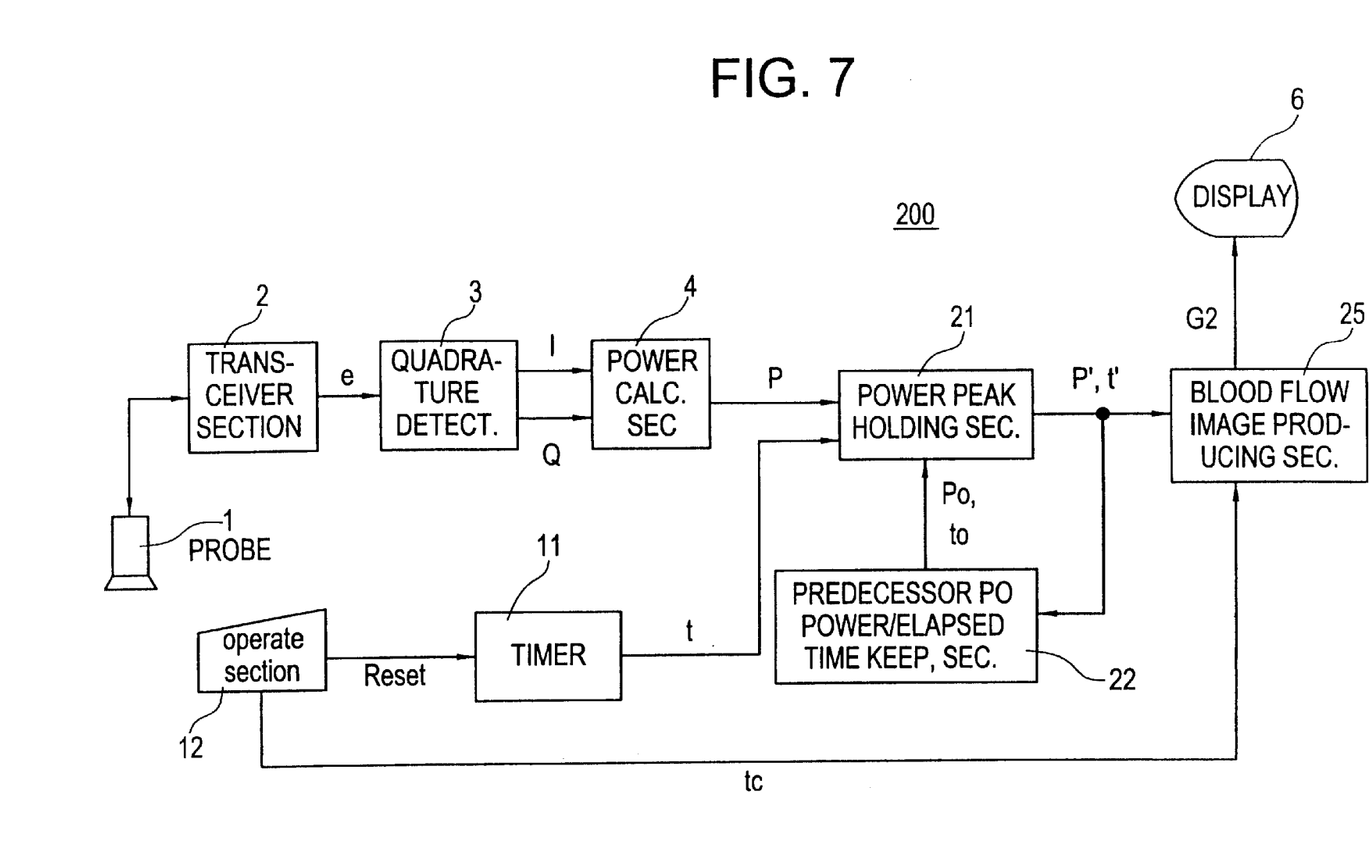
FIG. 7 is a block diagram showing an ultrasonic diagnostic apparatus in accordance with a second embodiment.

FIG. 7 is a block diagram showing an ultrasonic diagnostic apparatus in accordance with a second embodiment of the present invention.

The ultrasonic diagnostic apparatus 200 comprises: an ultrasonic probe 1; a transceiver section 2; a quadrature detector section 3; a power calculating section 4 for calculating the power P of blood flow; a power peak holding section 21 for comparing the latest power P and a predecessor peak value Po, and outputting the larger one as a peak value P' and an elapsed time t' corresponding to the peak value P'; a predecessor power/elapsed time keeping section 22 for keeping the predecessor peak value Po and the corresponding elapsed time 'to' and outputting these values to the power peak holding section 21; a timer 11 for measuring an elapsed time t from a reference time; a blood flow image producing section 25 for producing a power peak hold blood flow image G2 in which the hue is changed before and after the elapsed time t' reaches a hue change time tc and the brightness varies depending upon the peak value P'; an operating section 12 for resetting the timer 11 and specifying the hue change time tc; and a display 6.

The power peak holding section 21 compares the latest power P and the predecessor peak value Po, and if P>Po, the section 21 outputs the power P as a peak value P' and an elapsed time t' corresponding to the power P. If P≦Po, the section 21 outputs the predecessor peak value Po as the peak value P' and an elapsed time t' corresponding to the predecessor peak value Po.

The blood flow image producing section 25 produces a power peak hold blood flow image G2 in which the hue of the blood flow is set to red if the elapsed time t'<tc and is set to blue if t'≧tc, and displays the image G2 on the display 6.

Figure 8:
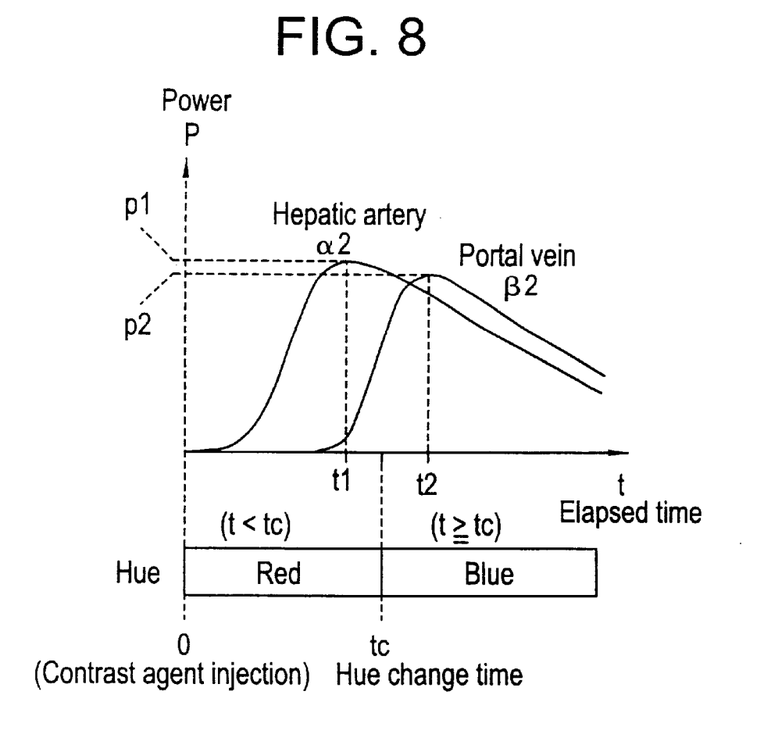
FIG. 8 is an explanatory diagram showing the relationship between the blood flow power properties and the hue of a blood flow image in the ultrasonic diagnostic apparatus of FIG. 7.

FIG. 8 shows an example of the properties of the power P of blood flow α2 in the hepatic artery and blood flow β2 in the portal vein, and the hue with respect to the elapsed time t.

An elapsed time t1 at which the power P of the blood flow α2 in the hepatic artery reaches a peak value p1 is t1<tc. The elapsed time t1 is, for example, 10 seconds. The hue change time tc is, for example, 12.5 seconds.

An elapsed time t2 at which the power P of the blood flow β2 in the portal vein reaches a peak value p2 is t2≧tc. The elapsed time t2 is, for example, 15 seconds.

Figure 9:
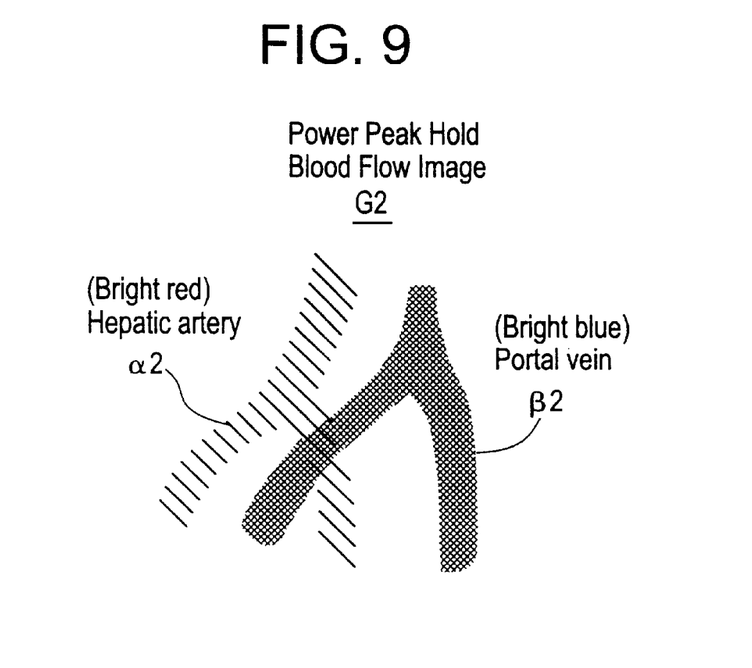
FIG. 9 is an explanatory diagram showing a blood flow image in a power peak hold mode in the ultrasonic diagnostic apparatus of FIG. 7.

Therefore, as shown FIG. 9, in the power peak hold blood flow image G2 after the elapsed time t2, the blood flow α2 in the hepatic artery continues to be displayed in bright red (i.e., at the brightness corresponding to the peak value p1), and in addition, the blood flow β2 in the portal vein is displayed in bright blue (i.e., at the brightness corresponding to the peak value p2).

According to the ultrasonic diagnostic apparatus 200 of the second embodiment, even if a time period in which a plurality of streams of blood flow are simultaneously infused with the contrast agent is long, a power peak hold blood flow image G2 can be displayed in which the hues of the blood flow streams are differentiated depending upon the difference of the time at which the power P of the blood flow reaches a peak value. For example, the hepatic artery blood flow α2 and the portal vein blood flow β2 can be displayed in different colors.

Third Embodiment

Figure 10:
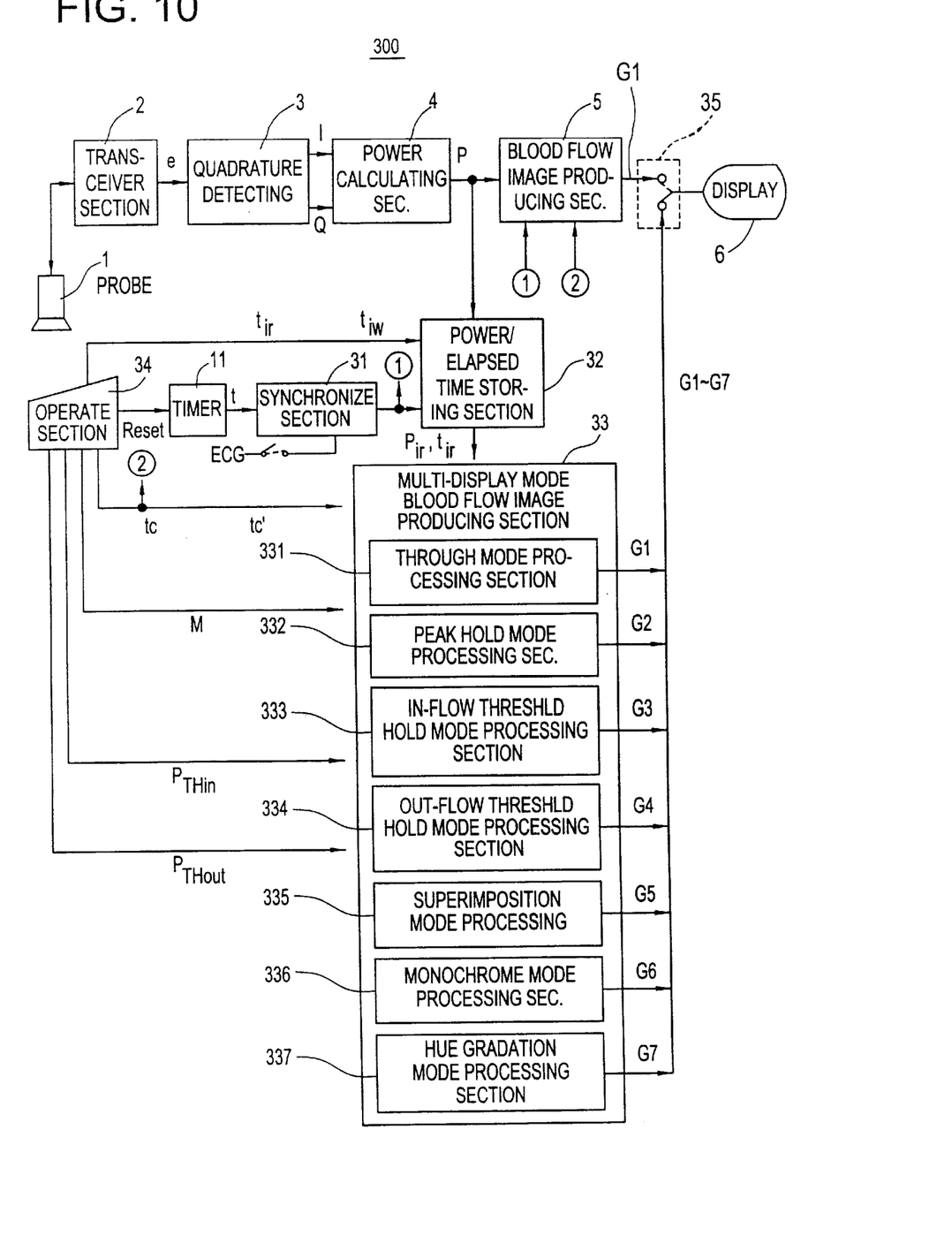
FIG. 10 is a block diagram showing an ultrasonic diagnostic apparatus in accordance with a third embodiment.

FIG. 10 is a block diagram showing an ultrasonic diagnostic apparatus in accordance with a third embodiment of the present invention.

The ultrasonic diagnostic apparatus 300 comprises: an ultrasonic probe 1; a transceiver section 2; a quadrature detector section 3; a power calculating section 4 for calculating the power P of blood flow; a timer 11 for measuring an elapsed time t from a reference time; a synchronization section 31 for resetting the elapsed time t synchronously with an R-wave supplied from an ECG (electrocardiograph); a blood flow image producing section 5 for producing a blood flow image G1 in which the hue is changed before and after the elapsed time t reaches a hue change time tc and the brightness varies depending upon the power P; a power/elapsed time storing section 32 for continuously recording the power P and the corresponding elapsed time t; a multi-display-mode blood flow image producing section 33 for producing blood flow images G1–G7 in several display modes; an operating section 34 having the functions which will be described below; a switch 35 for selecting between outputs from the blood flow image producing section 5 and the multi-display-mode blood flow image producing section 33; and a display 6.

The operating section 34 receives instructions from the operator, and resets the timer 11. The section 34 also outputs a hue change time tc, a gradation change time tc', a display mode selection signal M, an in-flow threshold $P_{THin}$ and an out-flow threshold $P_{THout}$ (the details of which will be described later). Moreover, the section 34 prescribes timing $T_{iw}$ for gathering the power P into the power/elapsed time storing section 32 before and during a scan. (The gathering may be performed throughout a scan.) Furthermore, the operating section 34 outputs a power readout time $t_{ir}$ for reading out a power $P_{ir}$ stored in the power/elapsed time storing section 32.

The multi-display-mode blood flow image producing section 33 comprises a through mode processing section 331, a peak hold mode processing section 332, an in-flow threshold hold mode processing section 333, an out-flow threshold hold mode processing section 334, a superimposition mode processing section 335, a monochrome mode processing section 336 and a hue gradation mode processing section 337. The operation of these mode processing sections will be described later.

The operation of the ultrasonic diagnostic apparatus 300 will now be described. The operation when the switch 35 selects the output from the blood flow image producing section 5 is the same as that of the ultrasonic diagnostic apparatus 100 (see FIG. 2) in accordance with the first embodiment, and explanation thereof will be omitted.

When the operator selects a display mode using the operating section 34, a display mode selection signal M is sent to the multi-display-mode blood flow image producing section 33.

When a through mode is selected, the power $P_{ir}$ for each pixel on a screen is read out for each frame from the power/elapsed time storing section 32, and a blood flow image G1 is produced at the through mode processing section 331. The blood flow image G1 is the same as that produced by the blood flow image producing section 5.

When a peak hold mode is selected, the power $P_{ir}$ is read out for each frame, and a blood flow image G2 is produced at the peak hold mode processing section 332. The blood flow image G2 is the same as that in the ultrasonic diagnostic apparatus 200 (see FIG. 7) in accordance with the second embodiment.

Figure 11:
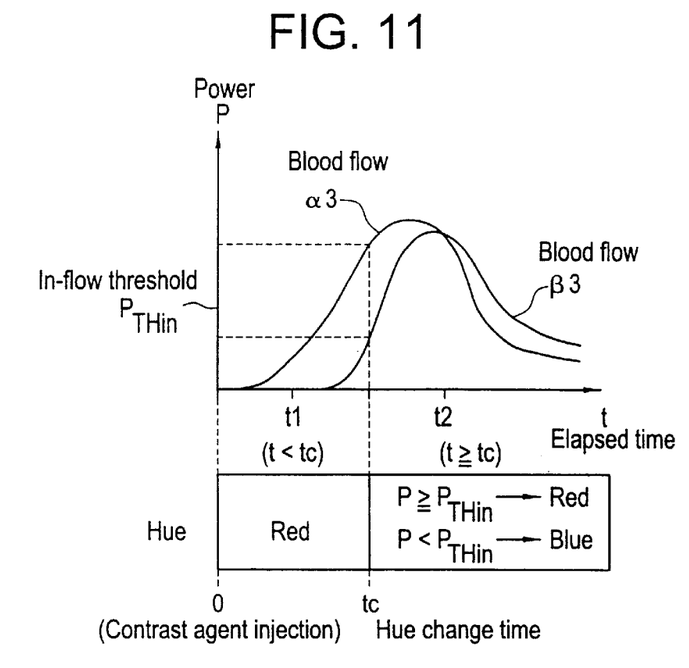
FIG. 11 is an explanatory diagram showing the relationship between the blood flow power properties and the hue of a blood flow image in a flow-in threshold hold mode.
Figure 12A:
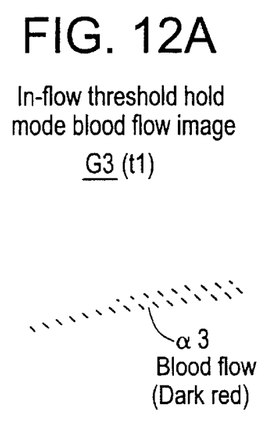
FIG. 12 is an explanatory diagram showing the transition of a blood flow image in the flow-in threshold hold mode.
Figure 12B:
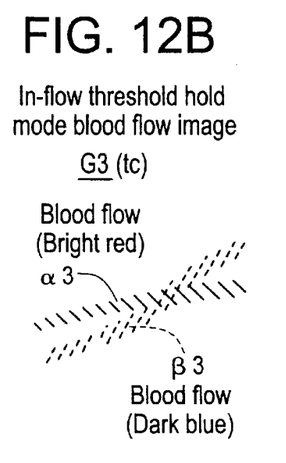
Figure 12C:
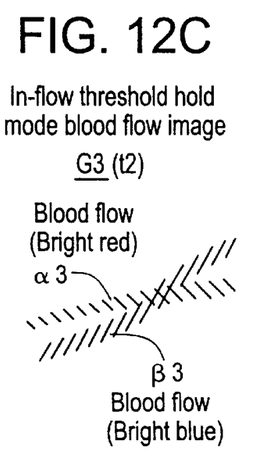

When an in-flow threshold hold mode is selected, the power $P_{ir}$ is read out for each frame, and an in-flow threshold hold mode blood flow image G3 is produced at the in-flow threshold hold mode processing section 333. As shown in FIG. 11, in the in-flow threshold hold mode, the hue change time tc is specified within a period in which the contrast agent flows in, and the hue is set to red in a blood flow reproduction period t<tc; the hue remains red in a blood flow reproduction period t≧tc if the power P≧in-flow threshold $P_{THin}$, and the hue is changed to blue if the power P<in-flow threshold $P_{THin}$. Therefore, when the blood flow at the elapsed time t=t1 (t1<tc) is reproduced, the blood flow α3 is displayed in dark red, as shown in FIG. 12(a). When the blood flow at the elapsed time t=tc is reproduced, the blood flow α3 is displayed in bright red and the blood flow β3 is displayed in dark blue, as shown in FIG. 12(b). When the blood flow at the elapsed time t=t2 (t2>tc) is reproduced, the blood flow α3 is displayed in bright red and the blood flow β3 is displayed in bright blue, as shown in FIG. 12(c). Thus, even if the times at which the powers P of the blood flow α3 and β3 reach peak values are close to each other, the blood flow α3 and β3 can be displayed in different colors depending upon whether or not the power P at the hue change time tc is equal to or larger than the in-flow threshold $P_{THin}$.

Figure 13:
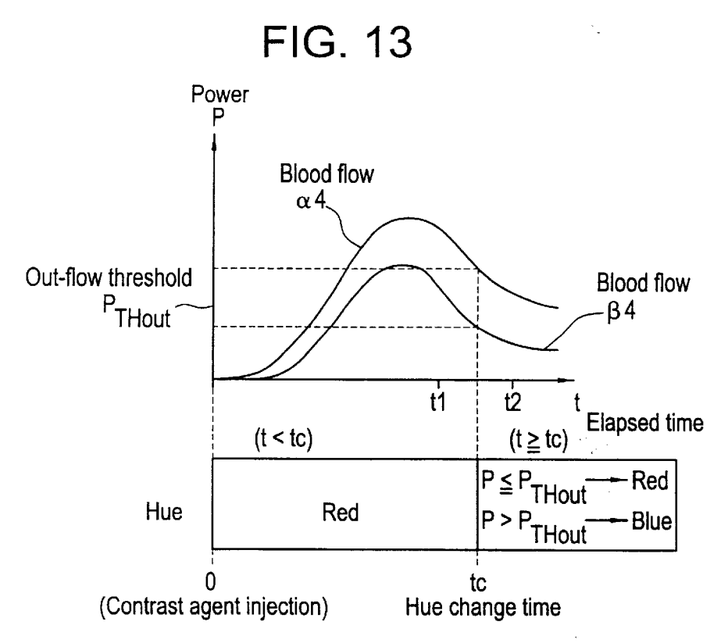
FIG. 13 is an explanatory diagram showing the relationship between the blood flow power properties and the hue of a blood flow image in a flow-out threshold hold mode.
Figure 14A:
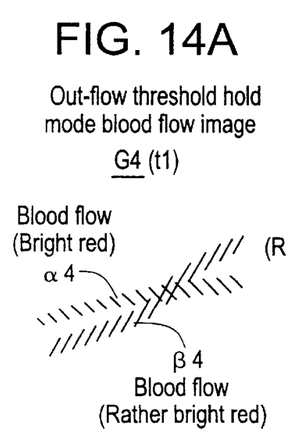
FIG. 14 is an explanatory diagram showing the transition of a blood flow image in the flow-out threshold hold mode.
Figures 14B, 14C:
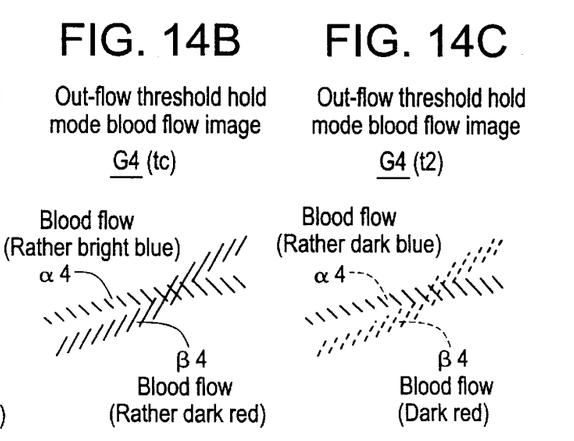

When an out-flow threshold hold mode is selected, the power $P_{ir}$ is read out for each frame, and an out-flow threshold hold mode blood flow image G4 is produced at the out-flow threshold hold mode processing section 334. As shown in FIG. 13, in the out-flow threshold hold mode, the hue change time tc is specified within a period in which the contrast agent flows out, and the hue is set to red in a blood flow reproduction period t<tc; the hue remains red in a blood flow reproduction period t≧tc if the power P≦out-flow threshold $P_{THout}$, and the hue is changed to blue if the power P>out-flow threshold $P_{THout}$. Therefore, when the blood flow at the elapsed time t=t1 (t1<tc) is reproduced, the blood flow α4 is displayed in bright red and the blood flow β4 is displayed in rather bright red, as shown in FIG. 14(a). When the blood flow at the elapsed time t=tc is reproduced, the blood flow α4 is displayed in rather bright blue and the blood flow β4 is displayed in rather dark red, as shown in FIG. 14(b). When the blood flow at the elapsed time t=t2 (t2>tc) is reproduced, the blood flow α4 is displayed in rather dark blue and the blood flow β4 is displayed in dark red, as shown in FIG. 14(c). Thus, even if the times at which the powers P of the blood flow α4 and β4 reach peak values are close to each other, the blood flow α4 and β4 can be displayed in different colors depending upon whether or not the power P at the hue change time tc is equal to or smaller than the out-flow threshold $P_{THout}$.

Figure 15A:
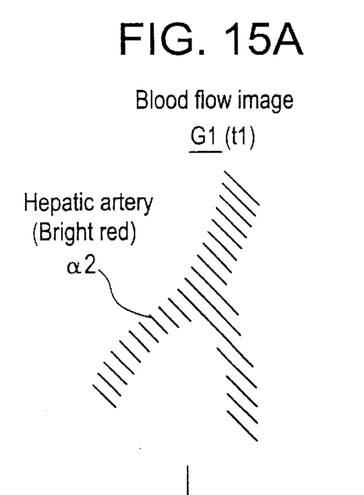
FIG. 15 is an explanatory diagram showing a blood flow image in a superimposition mode.
Figure 15B:
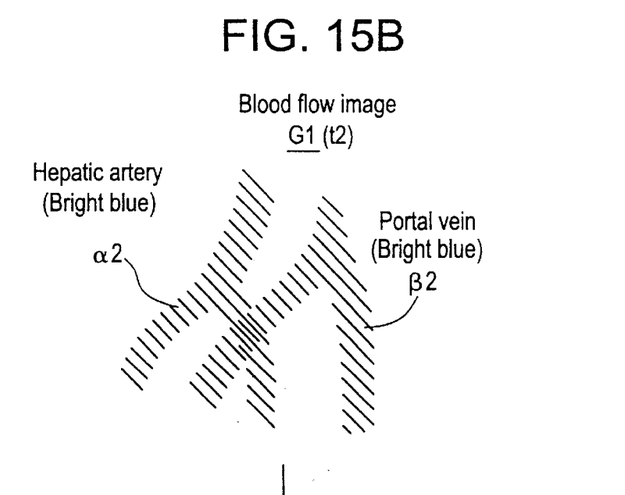
Figure 15C:
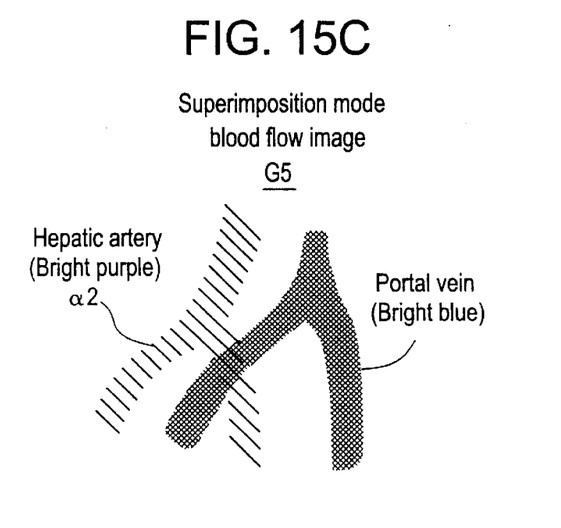

When a superimposition mode is selected, a power $P_{ir}$ and a power readout time $t_{ir}$ corresponding to the elapsed times t1 and t2 specified by the operator are read out from the power/elapsed time storing section 32, and sent to the superimposition mode processing section 335. The superimposition mode processing section 335 produces blood flow images G1(t1) and G1(t2) corresponding to the elapsed times t1 and t2 by processing similar to that in the blood flow image producing section 5, and produces a superimposition mode blood flow image G5 in which the blood flow images G1 are superimposed. For example, the hepatic artery blood flow α2 and the portal vein blood flow β2 having such power properties as exemplified in FIG. 8 are to be displayed, the hue of the hepatic artery blood flow α2 in the blood flow image G1(t1) is bright red, as shown in FIG. 15(a). The hues of the hepatic artery blood flow α2 and the portal vein blood flow β2 in the blood flow image G1(t2) are bright blue, as shown in FIG. 15(b). Therefore, the superimposition mode blood flow image G5 is a still image with the hepatic artery blood flow α2 displayed in bright purple (i.e., by additive mixing of bright red and blue), and with the portal vein blood flow β2 displayed in bright blue, as shown in FIG. 15(c). It should be noted that, if the superimposition is achieved by a simple addition on display values, the resulting display value may saturate; and therefore normalization is applied so that the display value falls within a normal range. Moreover, the superimposition region having different hues (the purple region in the above example) may be displayed in a hue different from one obtained by the additive mixing (e.g., in yellow).

When a monochrome mode is selected, the power $P_{ir}$ is read out for each frame, and a monochrome mode blood flow image G6 is produced at the monochrome mode processing section 336.

Figure 16:
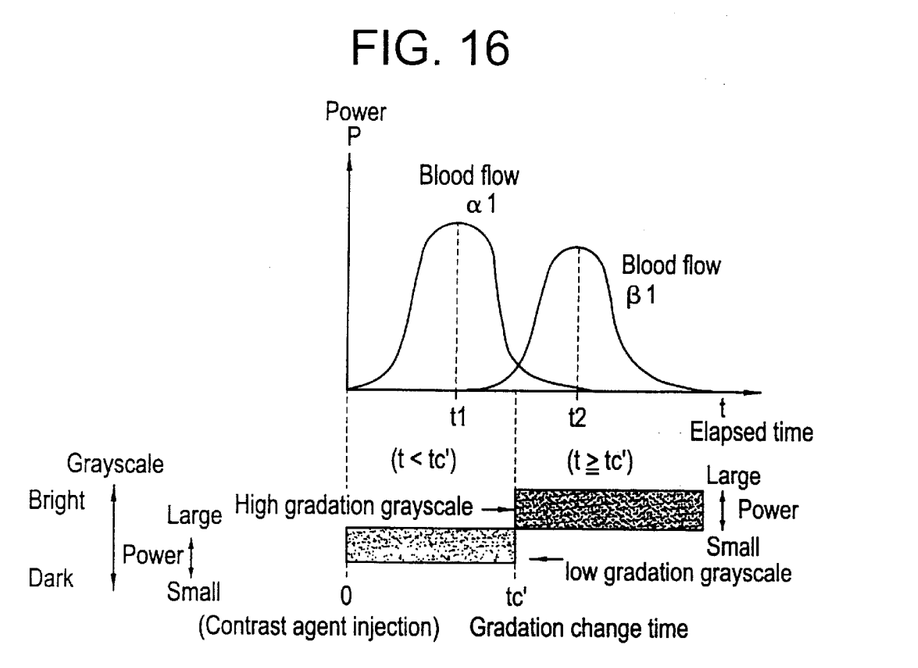
FIG. 16 is an explanatory diagram showing the relationship between the blood flow power properties and the gradation of a blood flow image in a monochrome mode.
Figure 17A:
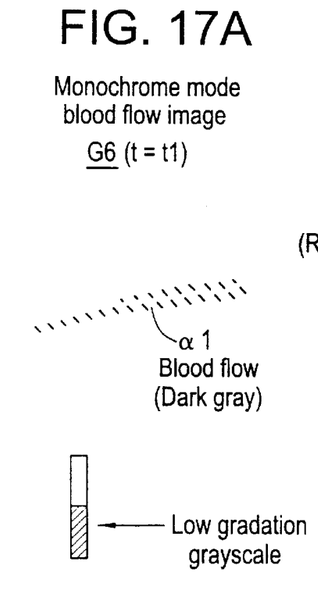
FIG. 17 is an explanatory diagram showing the transition of a blood flow image in the monochrome mode.
Figure 17B:
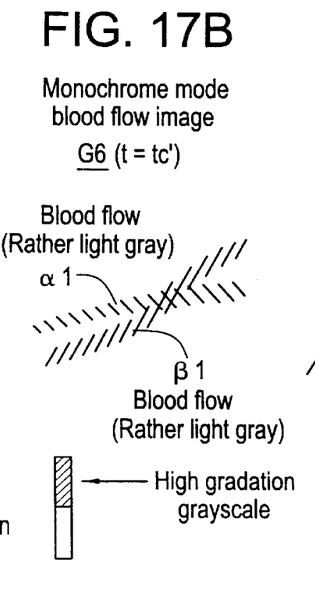
Figure 17C:
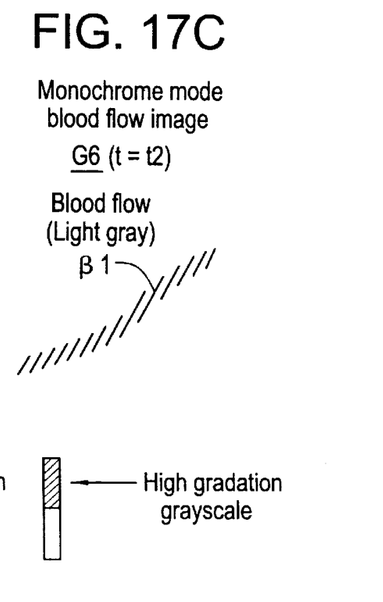

As shown in FIG. 16, in the monochrome mode, a grayscale having 256 gradations, for example, is divided into two gradation ranges including a low gradation grayscale and a high gradation grayscale. The low gradation grayscale is used for representing blood flow before the elapsed time t reaches the gradation change time tc', and the high gradation grayscale is used for representing blood flow after the elapsed time t has reached gradation change time tc'. Therefore, when the blood flow at the elapsed time t=t1 (t1<tc') is reproduced, the blood flow α1 is displayed in dark gray, as shown in FIG. 17(a). When the blood flow at the elapsed time t=tc' is reproduced, the blood flow α1 and β1 are displayed in rather light gray, as shown in FIG. 17(b). When the blood flow at the elapsed time t=t2 (t2>tc) is reproduced, the blood flow β1 is displayed in light gray, as shown in FIG. 17(c). Thus, the blood flow α1 and β1 can be properly discerned even in a monochrome image by using different grayscales before and after the gradation change time tc'.

When a hue gradation mode is selected, the power $P_{ir}$ is read out for each frame, and a hue gradation mode blood flow image G7 is produced at the hue gradation mode processing section 337.

Figure 18:
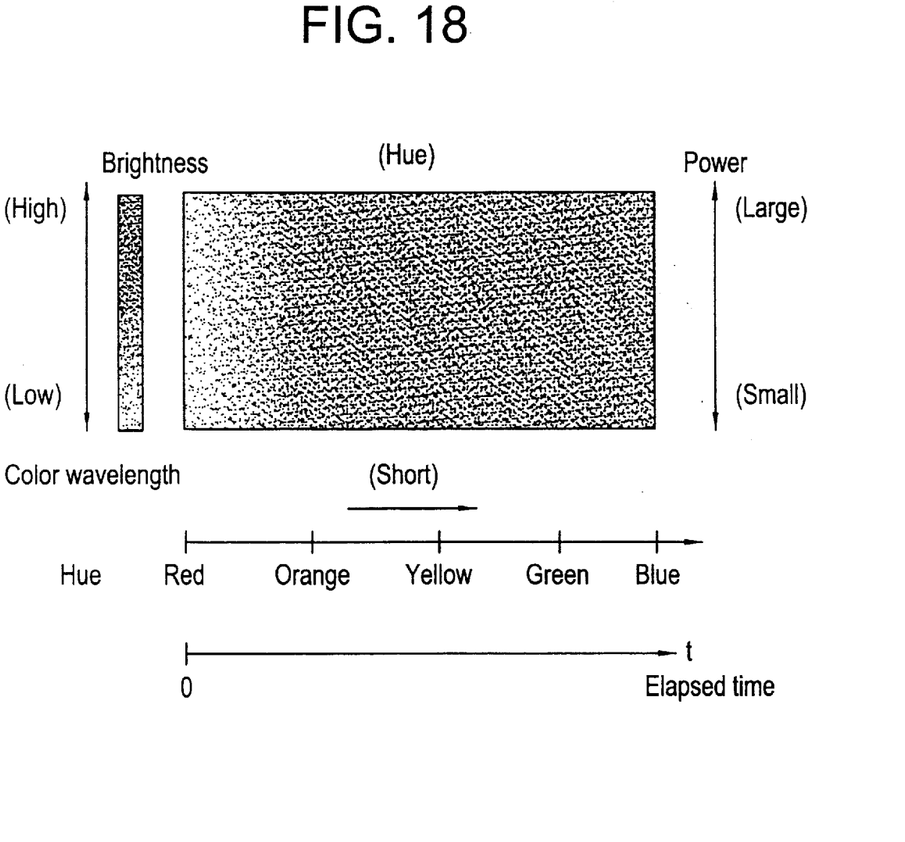
FIG. 18 is an explanatory diagram showing the hue of a blood flow image in a hue gradation mode.

As shown in FIG. 18, in the hue gradation mode, the hue is changed in multicolor with respect to the elapsed time t to display the blood flow. Specifically, the blood flow at the elapsed time t=0 is displayed in red, and the wavelength representing the hue becomes shorter with the elapsed time t. Thus, a plurality of streams of blood flow having different times of infusion by the contrast agent can be properly discerned from the variation in hue.

When the blood flow image is displayed using the multi-display-mode blood flow image producing section 33, the specification and change of the hue change time tc, gradation change time tc', in-flow threshold $P_{THin}$, out-flow threshold $P_{THout}$, power readout time $t_{ir}$ and display mode may be performed in any period before, during or after scanning. Therefore, if the power property of the blood flow is different among types of the contrast agent and among subject individuals, a blood flow image suitable for interpretation by a physician can be displayed.

According to the ultrasonic diagnostic apparatus 300 of the third embodiment, a blood flow image G1 produced at the blood flow image producing section 5 can be displayed in real time. Moreover, blood flow images G1–G7 can be produced in several display modes (through mode, peak hold mode, in-flow threshold hold mode, out-flow threshold hold mode, superimposition mode, monochrome mode and hue gradation mode) even after scanning by reading the power $P_{ir}$ etc. stored in the power/elapsed time storing section 32, and therefore a blood flow image suitable for interpretation by a physician can be displayed. Furthermore, the blood flow images G1–G7 can be produced to match the cardiac cycle by resetting the elapsed time t synchronously with an ECG.

Other Embodiments

The present invention is not limited to power Doppler blood flow imaging, but may be applied to blood flow imaging by a B-mode or ultrasonic harmonic technique.

Moreover, the present invention is not limited to an ultrasonic imaging apparatus, but may be generally applied to blood flow imaging apparatuses such as those for X-ray angiography, CT (computed tomography) angiography and MR (magnetic resonance) angiography. It should be noted that, in the X-ray angiography, the contrast agent can be applied to an arbitrary site using a catheter inserted into the subject, and therefore the hue and brightness of the blood flow may be changed corresponding to different times of possible infusion of the blood flow by the contrast agent, instead of corresponding to the elapsed time t (i.e., the time period after the contrast agent is intravenously injected).

Many widely different embodiments of the invention may be configured without departing from the spirit and the scope of the present invention. It should be understood that the present invention is not limited to the specific embodiments described in the specification, except as defined in the appended claims.

What is claimed is:

1. A blood flow imaging method for scanning and detecting blood flow infused with a contrast agent injected into a subject, and displaying the blood flow, comprising the steps of:
   changing at least one of a hue and a gradation range of a display region representing said blood flow of at least one stream of blood flow in one or more steps and in course of time.

2. The method of claim 1, further comprising the step of displaying said at least one stream of blood flow having different times at which blood flow detection intensity reaches a peak value in different hues and gradation ranges.

3. The method of claim 1, further comprising the steps of producing a plurality of blood flow images corresponding to different times in different changed hues or gradation ranges; and displaying a blood flow image in which said plurality of blood flow images are superimposed.

4. A blood flow imaging apparatus comprising:
   scanning means for scanning a subject to detect blood flow infused with a contrast agent;
   image means for producing a blood flow image in which at least one of a hue and a gradation range of a display region representing blood flow is changed in one or more steps in course of time; and
   display means for displaying said blood flow image.

5. The apparatus of claim 4, wherein said image means comprises means for producing a blood flow image wherein a plurality of streams of blood flow having different times at which blood flow detection intensity reaches a peak value are represented in different hues or gradation ranges.

6. The apparatus of claim 4, wherein said image means comprises means for producing a plurality of blood flow images corresponding to different times in different hues or gradation ranges, and means for producing a blood flow image wherein said plurality of blood flow images are superimposed.

7. The apparatus of claim 4, wherein said image means comprises means for producing blood flow image synchronously with an electrocardiogram.

8. An ultrasonic diagnostic apparatus comprising:

an ultrasonic probe;

a transceiver means for transmitting ultrasound from said ultrasonic probe, for acquiring an ultrasonic echo, and outputting a received signal based on said ultrasonic echo;

image means for producing a blood flow image wherein at least one of a hue and a gradation range of a display region representing blood flow infused with a contrast agent is changed in one or more steps in course of time; and display means for displaying said blood flow image.

9. The apparatus of claim 8, wherein said image means comprises means for producing a blood flow image wherein a plurality of streams of blood flow having different times at which blood flow detection intensity reaches a peak value are represented in different hues or gradation ranges.

10. The apparatus of claim 8, wherein said image means comprises means for producing a plurality of blood flow images corresponding to different times in different hues or gradation ranges, and means for producing a blood flow image wherein said plurality of blood flow images are superimposed.

11. The apparatus of claim 8, wherein said image means comprises means for producing blood flow image synchronously with an electrocardiogram.

12. A blood flow imaging method for scanning and detecting blood flow infused with a contrast agent injected into a subject, and displaying the blood flow, comprising the steps of:

changing at least one of a hue and a gradient range of a display region representing said blood flow of at least one stream of blood flow in one or more steps in course of time;

displaying said blood flow of said at least one stream of blood flow in a predefined hue or gradation range of before a hue or gradation range change time specified within a contrast agent flow-in or flow-out period; and displaying, after said hue or gradation range time change, said blood flow in a hue or gradation range determined by relationship between a blood flow detection intensity and an in-flow or out-flow threshold at said hue or gradation range change time.

13. The method of claim 12, wherein said displaying said at least one stream of blood flow is of blood flow having different times at which blood flow detection intensity reaches a peak value in different hues or gradation ranges.

14. The method of claim 12, further comprising the steps of:

producing a plurality of blood flow images corresponding to different times in different changed hues or gradation ranges; and displaying a blood flow image in which said plurality of blood flow images are superimposed.

15. A blood flow imaging apparatus comprising:

scanning means for scanning a subject to detect blood flow infused with a contrast agent;

image means for producing a blood flow image in which at least one of a hue and a gradation range of a display region representing blood flow is changed in one or more steps in course of time;

display means for displaying said blood flow image; and specifying means for use by an operator to specify a hue or gradation range change time within a contrast agent in-flow or out-flow period; wherein said image means comprises means for producing a blood flow image wherein blood flow is represented in a predefined hue or gradation range before said hue or gradation range change time, and means for producing a blood flow range wherein said blood flow is presented after said hue or gradation range change time, in a hue or gradation range determined by relationship between a blood flow detection intensity and an in-flow or out-flow threshold at said hue or gradation range change time.

16. The apparatus of claim 15, wherein said image means comprises means for producing a blood flow image wherein a plurality of streams of blood flow having different times at which blood flow detection intensity reaches a peak value, are represented in different hues or gradation ranges.

17. The apparatus of claim 15, wherein said image means comprises means for producing a plurality of blood flow images corresponding to different times in different hues or gradation ranges, and means for producing a blood flow image wherein said plurality of blood flow images are superimposed.

18. The apparatus of claim 15, wherein said image means comprises means for producing blood flow image synchronously with an electrocardiogram.

19. An ultrasonic diagnostic apparatus comprising:

an ultrasonic probe;

a transceiver means for transmitting ultrasound from said ultrasonic probe, for acquiring an ultrasonic echo, and outputting a received signal based on said ultrasonic echo;

image means for producing a blood flow image wherein at least one of a hue and a gradation range of a display region representing blood flow infused with a contrast agent is changed in one or more steps in course of time;

display means for displaying said blood flow image; and specifying means for use by an operator to specify a hue or gradation range change time within a contrast agent in-flow or out-flow period; wherein said image means comprises means for producing a blood flow image wherein said blood flow is represented in a predefined hue or gradation range before said hue or gradation range change time, and means for producing a blood flow image wherein said blood flow is represented, after said hue or gradation range change time, in a hue or gradation range determined by an in-flow or out-flow threshold at said hue or gradation range change time.

20. The apparatus of claim 19 wherein said image means comprise means for producing a blood flow image wherein a plurality of streams of blood flow having different times at which blood flow detection intensity reaches a peak value, are represented in different hues or gradation ranges.

21. The apparatus of claim 19, wherein said image means comprises means for producing a plurality of blood flow images corresponding to different times in different hues or gradation ranges, and means for producing a blood flow image wherein said plurality of blood flow images are superimposed.

22. The apparatus of claim 19, wherein said image means comprise means for producing a image synchronously with an electrocardiogram.

* * * * *